US011019867B2

(12) United States Patent
Marco

(10) Patent No.: US 11,019,867 B2
(45) Date of Patent: Jun. 1, 2021

(54) HAT FOR SECURING EXTERNAL HARDWARE OF A COCHLEAR IMPLANT

(71) Applicant: Cecelia Ann Marco, Riley Township, MI (US)

(72) Inventor: Cecelia Ann Marco, Riley Township, MI (US)

(*) Notice: Subject to any disclaimer, the term of this patent is extended or adjusted under 35 U.S.C. 154(b) by 623 days.

(21) Appl. No.: 14/544,733

(22) Filed: Feb. 9, 2015

(65) Prior Publication Data
US 2015/0223539 A1    Aug. 13, 2015

Related U.S. Application Data

(60) Provisional application No. 61/965,913, filed on Feb. 10, 2014.

(51) Int. Cl.
*A42B 1/045* (2021.01)
*A42B 1/0188* (2021.01)

(52) U.S. Cl.
CPC ............ *A42B 1/045* (2013.01); *A42B 1/0188* (2021.01)

(58) Field of Classification Search
CPC ......... A42B 1/068; A42B 1/045; A42B 1/008; A42B 1/066; A42B 3/033; A42B 1/0188; A42C 5/04
USPC ............. 362/106; 2/172, 207, 204, 206, 412
See application file for complete search history.

(56) References Cited

U.S. PATENT DOCUMENTS

| 2,143,265 | A | * | 1/1939 | Goldstein | A42B 1/066 2/172 |
|---|---|---|---|---|---|
| 2,743,454 | A | * | 5/1956 | Woodbury | A42B 1/068 2/172 |
| 3,932,897 | A | | 1/1976 | Young | |
| 4,205,406 | A | | 6/1980 | Wangkeo et al. | |
| 5,282,766 | A | | 2/1994 | Fleet | |
| 5,685,466 | A | | 11/1997 | Hsieh | |
| 5,822,800 | A | * | 10/1998 | Anderson | A42B 1/041 2/171 |
| 5,881,390 | A | * | 3/1999 | Young | A41D 20/00 2/209.13 |
| 6,360,376 | B1 | * | 3/2002 | Carrington | A42B 3/00 2/411 |

(Continued)

OTHER PUBLICATIONS

Silkawear, Mar. 12, 2008, http://www.silkawear.com.*

(Continued)

*Primary Examiner* — Khoa D Huynh
*Assistant Examiner* — Abby M Spatz
(74) *Attorney, Agent, or Firm* — Christopher John Rudy

(57) ABSTRACT

A hat having a body of conforming material to cover at least a portion of a wearer's head and at least generally encircle the head about a forehead or upper crown, and a depending projection on at least one side having a lower boundary lower than a respective ear lobe of the wearer; an opposing pair of substantially wide under chin straps of conforming material attached to lower left and right boundaries of the body, the straps being fastened with a non-tying securing couple fixed to the under chin straps; and, in part of the depending projection, a soft, conforming open mesh to cover the external hardware of a cochlear implant or a traditional hearing aid, and provide for securing of the same when worn by the wearer and for external visibility of the same by a non-wearer of the hat. The wearer may be a young child.

19 Claims, 5 Drawing Sheets

(56) References Cited

U.S. PATENT DOCUMENTS

| | | | |
|---|---|---|---|
| 6,408,468 | B1 | 6/2002 | Comfort |
| 6,560,488 | B1 | 5/2003 | Crawford ..................... 607/56 |
| 6,905,096 | B1 | 6/2005 | Tabor et al. |
| 7,024,703 | B1 | 4/2006 | Della Ratta |
| 8,201,960 | B2 | 6/2012 | Ortega |
| 8,627,520 | B1 | 1/2014 | Morton |
| 9,173,439 | B2 | 11/2015 | Gray |
| 9,326,641 | B2 | 5/2016 | Murphy |
| 9,351,085 | B2 | 5/2016 | Hojlund et al. |
| 9,375,375 | B2 | 6/2016 | Wang |
| 9,399,164 | B2 | 7/2016 | Maier |
| 2005/0066421 | A1* | 3/2005 | Brundage ............... A42C 5/00 2/209.3 |
| 2008/0022441 | A1* | 1/2008 | Oranchak ............. A42B 1/242 2/410 |
| 2009/0193564 | A1* | 8/2009 | Niedrich ........... A41D 13/1184 2/173 |
| 2009/0241239 | A1* | 10/2009 | Reynolds .............. A42B 1/206 2/172 |
| 2010/0263167 | A1 | 10/2010 | Fox ................................ 16/400 |
| 2014/0177890 | A1 | 6/2014 | Hojlund et al. |

OTHER PUBLICATIONS

O'Reilly, R., KidsHeatth.org, "Cochler Implants," Sep. 2012A.D.,6 pp.
Spencer, L., The ASHA Leader (www.asha.org), "Cochlear Implants in Infants and Toddlers," Jun. 16, 2009,5,7 pp.
Misc. hardware and hats, including Etsy.com Custom Pilot Cap, wih comments, Jan. 2014 A.D., 5 pp.
Haris, N. "The Safety of Children's Hats," www.livestrong.com, Feb. 6, 2013 A.D., 9 pp.
Boys Town National Research Hospital, "My Baby's Hearing . . . How can I help my baby adjust to hearing aids?" www.babyhearing.org, printed Feb. 8, 2014, 5 pp.
Ear Gear , www.gearforears.com, Custom Ear Gear Designs, Create the Ear Gear of Your Dreams, 1 p.
Marco, C., U.S. Appl. No. 61/965,913, filed Feb. 10, 2014 A.D.
USPTO Patent Full-Text and Image Database, Patent Database Search Results, ACLM/"soft mesh" and Spec/soft, 7 patents, hits 1-7, Aug. 29, 2016.
USPTO Patent Full-Text and Image Database, Patent Database Search Results, ACLM/"soft fabric" and Spec/soft, 201 patents, hits 1-201, Aug. 29, 2016.
USPTO Patent Full-Text and Image Database, Patent Database Search Results, ACLM/"light weight" and ACLM/fleece, 2 patents, hits 1-2, Aug. 29, 2016.
USPTO Patent Full-Text and Image Database, Patent Database Search Results, ACLM/whimsical, 31 patents, hits 1-31, Aug. 29, 2016.
Wikipedia, the free encyclopedia, Coolmax, last modified Aug. 12, 2016, 2 pages, printed Sep. 1, 2016.
U. of Mich. Cochlear Implant Program handout, "Cochlear Implant use ALL waking hours!" citing Gifford, R., and Rossi (2003).
Mish et al., Merriam-Webster Inc., Webster's Ninth New Collegiate Dictionary, pp. 298, 299 and 443, 1984.
Biomedical Engineering, Free CSS Templates, "Traditional Hearing Aid," http://biomedicalengineering.yolasite.com/traditional-hearing-aid.php, printed Jun. 8, 2017.
Wikimedia Foundation, Inc., Wikipedia, "Hearing Aid," https://en.wikipedia.org/wiki/Hearing_aid, edited Jun. 2, 2107, printed Jun. 8, 2017.
USPTO Patent Full-Text and Image Database, Patent Database Search Results: "traditional hearing aid" in US Patent Collection, hit list of hits 1-58 of 58, Jun. 9, 2017.

\* cited by examiner

HAT FOR SECURING EXTERNAL HARDWARE OF A COCHLEAR IMPLANT

This claims benefits under 35 USC 119(e) of U.S. provisional No. 61/965,913 filed on Feb. 10, 2014 A.D. The specification of that application, of course, to include its drawings, is incorporated herein by reference in its entirety.

FIELD AND PURVIEW OF THE INVENTION

This concerns a hat for securing external hardware of a cochlear implant, notably of a child. Use of the hat to secure such hardware can also be of concern.

BACKGROUND TO THE INVENTION

Cochlear implants are some of the most marvelous medical devices offered by modern medicine. With such implants, which also may be known as "bionic ears," people who could not hear are given hearing, and hope. This includes young children.

Typically, the implant is made up of an implant package, which is secured inside or to the skull; and a sound and speech processor, which is worn externally, and which may be termed, "external hardware." The implant package has a receiver-stimulator with necessary electronic circuits; an antenna, which receives signals from a transmitter component of the sound and speech processor; a magnet, which holds the transmitter component over the antenna; and electrodes inserted into the cochlea to stimulate the hearing nerve much like a normal cochlear hair would do. The heart of the sound and speech processor is a minicomputer, which processes sound into digital information and sends it to the transmitter component for communication to the antenna and hence to the electrodes. The external hardware can resemble a common over the ear hearing aid in appearance, typically with a wire connection to the transmitter component. See, e.g., O'Reilly, The Nemours Foundation, "Cochlear Implants," a 2012 "kidshealth" online article. The external hardware can include a signal such a light so that a person may observe it while being worn by the wearer and ascertain if it is operating or not.

Cochlear implants are a huge investment in money, surgical impact, and parental commitment. It is generally accepted if not proven that the longer the child keeps his external hardware on—the faster hearing improvement occurs. The object is to wear it.

Difficulties can ensue in wearing the external hardware from sudden movements, falls or other impacts, which can disconnect the transmitter component from the antenna, and, especially predictable for small children at nearly any time or other persons during hours of sleeping or during a period of distraction, touching or removing the external hardware with a free hand. In the case of small children in particular, who may gain access to a battery of the external hardware, removal and ingestion of a toxic battery may occur. In addition, a parent or guardian may have a need to ascertain if the external hardware is operating through the signal light to determine if hearing is possible. Compare, Spencer, The ASHA Leader, "Cochlear Implants in Infants and Toddlers," a 2009 "asha" online article.

In attempted address of such problems so-called pilot hats have been employed. These hats, which resemble in appearance classic air corps headgear, are made of a light, soft material, and cover the skull and ears fairly snugly. Typically, they are made from a three-panel pattern, and are secured under the chin with a pair of tie straps. They are, however, of limited success, and problems continue and are even generated with their use. For example, it is difficult to determine if the external hardware has become upset or is operating, and the external hardware, if not the wearer himself, can overheat, causing a possibility of technical failure of the implant, and the propensity of the wearer, particularly a small child, to reach for, touch, grab, scratch, and perform any of a number of other actions adverse to the stability or operation of the implant through its external hardware. As well, such a hat can interfere with the incoming sound itself.

Although not necessarily prior art to the present invention, certain pilot hats have been modified with athletic mesh generally replacing an entire panel from lower seam to crown panel for wearing by infants with bionic ear(s). One such pilot hat had its tie straps modified with under the chin snap straps. Note, a corresponding "etsy" online article.

One of the main drawbacks to pilot hats is their ties. Parents often double tie them to keep children from removing the hat, which could present a safety issue should a child become entangled while wearing the hat. Note, Haris, "The Safety of Children's Hats," a Feb. 6, 2013 "livestrong" online article. Then, too, the hats are not stylish.

Other expedient measures have been tried to help hold external hardware in place in addition to sizing of equipment, from toupee tape, which, however, must be changed often and may irritate, to eyeglass bands and soft rubber rings around the equipment and ear, which are not highly effective and, too, may be a cause for irritation. Compare, Boys Town, "My Baby's Hearing, Hearing and Amplification," a "babyhearing" online article.

In addition, traditional hearing aids can present similar problems. Young children especially may reach for and remove unsecured traditional hearing aids.

It would be desirable to improve the art and reliably ameliorate if not solve one or more of the difficulties or obstacles attendant to wearing the hardware that accompanies a cochlear implant. It would be desirable to provide the art with an alternative.

A DISCLOSURE OF THE INVENTION

Provided is a hat for securing external hardware of a cochlear implant or traditional hearing aid of a wearer, which comprises a body of conforming material to cover at least a portion of the wearer's head and at least generally encircle the head about a forehead or a crown portion, and a depending projection on at least one side having a lower boundary lower than a respective ear lobe of the wearer; an opposing pair of substantially wide under-chin straps of conforming material attached to lower left and right boundaries of the body, the straps being fastened with a non-tying securing couple fixed to the under chin straps; and, in part of the depending projection a soft, conforming open mesh to cover the external hardware of the cochlear implant and provide for securing of the same when worn by the wearer and for external visibility of the same by a non-wearer of the hat. The present hat, in general, conforms to the wearer such that he or she is discouraged from inserting his or her hand under the hat and removing the external hardware of the cochlear implant. The body may have the conforming material of soft fabric, for example, and it may span from front to back to cover the wearer's head from high forehead to crown to lower hairline/upper neck and over left and right have opposing sides with lower left and right boundaries lower than the wearer's ear lobes. The body may have or include as the conforming material, for example, fabric found in a child's fleece or cotton hat, baseball cap, or visor, which may already include the at least one depending projection, or two of them, as in various fleece hats, or may have the at least one depending projection, or two of them, added such as to the baseball cap or visor.

The invention is useful in helping in wearing external hearing assisting hardware.

Significantly, by the invention, the art is advanced in kind. Notably, one or more of the difficulties or obstacles attendant to the wearing of external hardware of cochlear implants, especially by young children, is reliably ameliorated, if not overcome. The art is provided with an alternative. With the present hat, comfort of the wearer as well as protection of his or her bionic ear(s) or traditional hearing aid(s) is exceedingly effective. It is very easy to determine if the external hearing hardware is upset or is operating, and the hat can reduce if not avoid overheating the external cochlear implant hardware. Thus, the possibility of technical failure of the cochlear implant can be addressed before it may otherwise occur, and the propensity of the wearer—for example, a small or young child, say, about three to five years of age or younger, or otherwise another person with mental capabilities of a young child—to reach for, touch, grab, scratch, and perform any of a number of other actions adverse to the stability or operation of the implant through its external hardware is reduced if not solved, and can assist in training him or her to not interfere or discard, but wear the hearing equipment. The hat has minimal if any practical interference with incoming sound itself. Inefficient and sometimes hazardous strap tying is avoided. The hat can be embodied with additional features to increase its efficiency and versatility. Specific colors, themes, and fabric designs can be employed to match or enhance the wearer's outfits, which can engender a desire to wear or continue wearing the hat, and so protect the hardware. The hat can be most aesthetically pleasing. The hat can be efficient to manufacture. Numerous further advantages attend the invention.

The drawings form part of the specification hereof. With respect to the drawings, which are not necessarily drawn to scale, the following is briefly noted:

FIG. 1 is a right, top perspective view of a toddler wearing his bionic ears secured by a hat for securing external hardware of a cochlear implant hereof. The hat is modified to be of a sole external layer of fleece and employs a fine, double layered mesh on its left and right side panels, only the right hand side portion being depicted, through which the secured external hardware can be seen. Material otherwise over the forehead can be trimmed, say, to the forward part of the wearer's crown, to keep the wearer cooler.

FIG. 2 is a plan view of a pattern for soft, conforming open mesh to cover the external hardware of the cochlear implant for a hat hereof, upon which is superimposed a scale in inches and a sample of a preferred open mesh, white mesh utility fabric obtained from a 10-yard bolt at Jo-Ann Fabric and Craft Stores, 100% polyester, No. 044 IN 13164 RN #35055, bar code/SKU No. 194-8439, 1787-10, which is advantageously employed in one layer only. The pattern is for modifying a boy's size 2-4T fleece hat (noting that "T sizes" are typically considered a toddler size).

FIG. 3 is plan view of a pattern for soft, conforming open mesh to cover the external hardware of the cochlear implant for a hat hereof, upon which is superimposed a scale in inches and a sample of an open mesh, less robust than that of depicted in FIG. 2, a blue mesh from a utility bag obtained from a discount store, which is preferably employed in a double layer. The pattern is for modifying a girl's 6-18 month fleece hat (noting that "month sizes" are typically considered an infant size).

Figure 1:
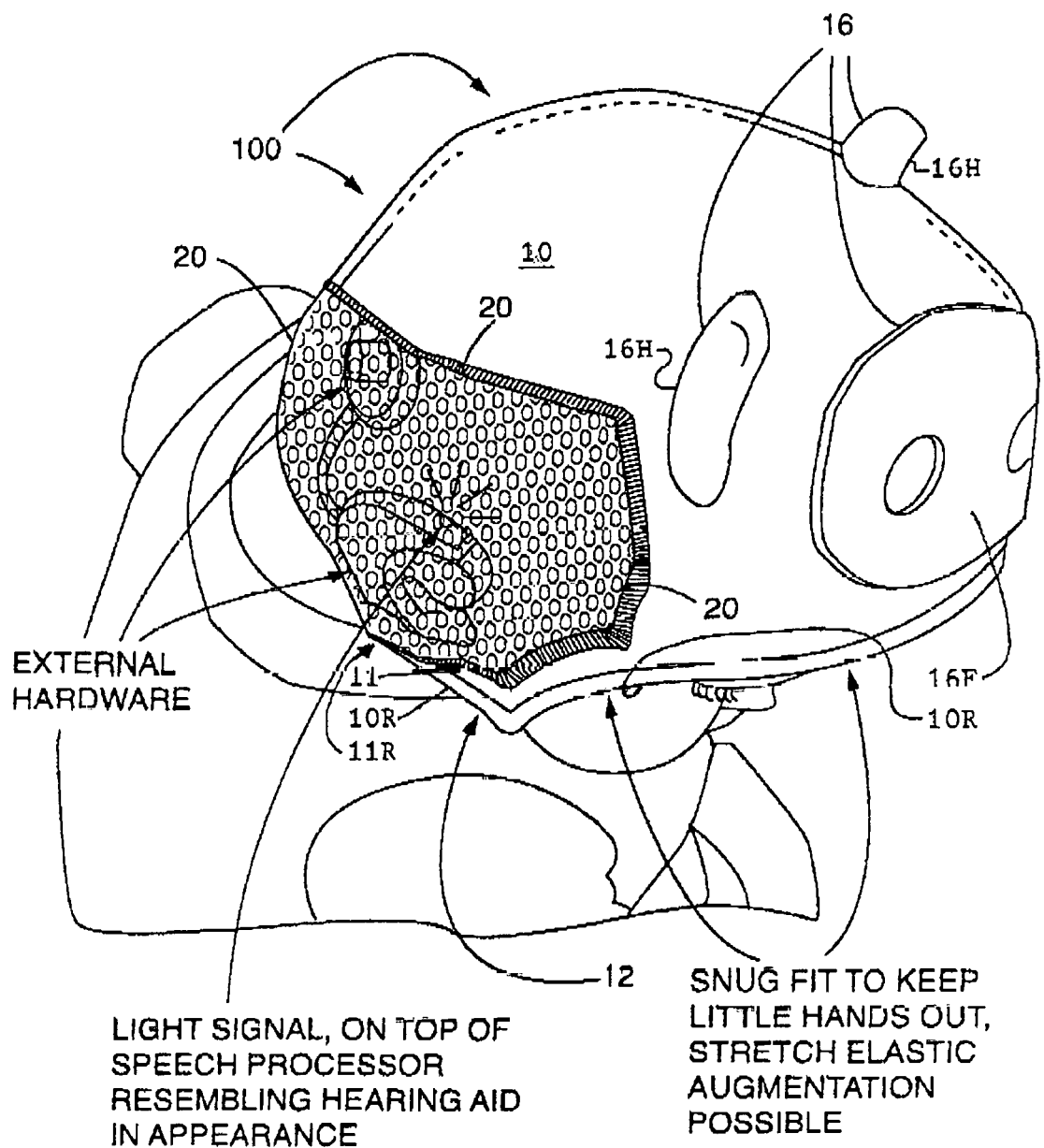

The invention can be further understood by the detail set forth below, which may be read in view of the drawings. The same, as with the foregoing, is to be taken in an illustrative and not necessarily limiting sense.

The type of hat forming a foundation for modification into the present hat may be considered to be an infant/toddler style hat. It may be provided with whimsical features such as soft cloth facial parts, stuffed horns, fleece pom-poms and so forth and the like to increase its aesthetic appeal, which may help to increase the desire to wear it. Other style hats may form a foundation for modification into the present hat. For example, a baseball cap or tennis type visor may be so modified.

Any suitable material(s) can be employed to make the present hat. For instance, a fleece material, advantageously a soft, light-weight, stretch fleece material, is a preferred material to make or from which is made the major portion of the hat. One layer of the fleece is preferred, which is beneficial for comfort indoors or even outdoors in moderate to cool weather. Other materials may be employed such as found in other caps of cotton, synthetic fabric, even wool and so forth, or a heavier material such as a heavier fleece may be employed especially for outdoor use in colder weather. A stretch material is advantageously employed. And, a fine to more open mesh, in one or more layer(s) may be employed. Any color of mesh may be used, but white or a light color may provide for having the external hearing hardware more readily observable by a parent or guardian.

The non-tying securing couple fixed to the under-chin straps may be any that is suitable. For example, a hook and loop system can be employed and/or a snap system may be employed. Another non-tying securing couple may be employed, itself or in addition to another non-tying securing couple, such as a non-tying securing couple having a magnetic component, a suction cup component, a suitably releasable adhesive, and so forth and the like.

Any suitable method(s) can be employed to make the hat. For instance, cutting and sewing are readily employed. Gluing may be employed.

With reference to the drawings, hat 100 which advantageously is for a young child—includes fleece hat body 10, fleece under-chin straps 12 with an affixed Velcro® hook and loop securing couple 14H, 14L, and whimsical features 16. Additional detail follows:

Numeral Comment
- 10B Bill of the hat body 10
- 10C Open crown of the hat body 10
- 10L Lower left boundary of the hat body 10
- 10R Lower right boundary of the hat body 10
- Depending projection portion of the hat body 10
- 11L Lower boundary of the left hand side depending projection portion 11
- 11R Lower boundary of the right hand side depending projection portion 11
- 12W Width of the under-chin straps 12
- 16E Feature representative of an ear as the whimsical feature 16
- 16F Feature representative of a facial part as the whimsical feature 16
- 16H Feature representative of a horn as the whimsical feature 16
- 16P Pom-pom as the whimsical feature 16.

Figure 2:
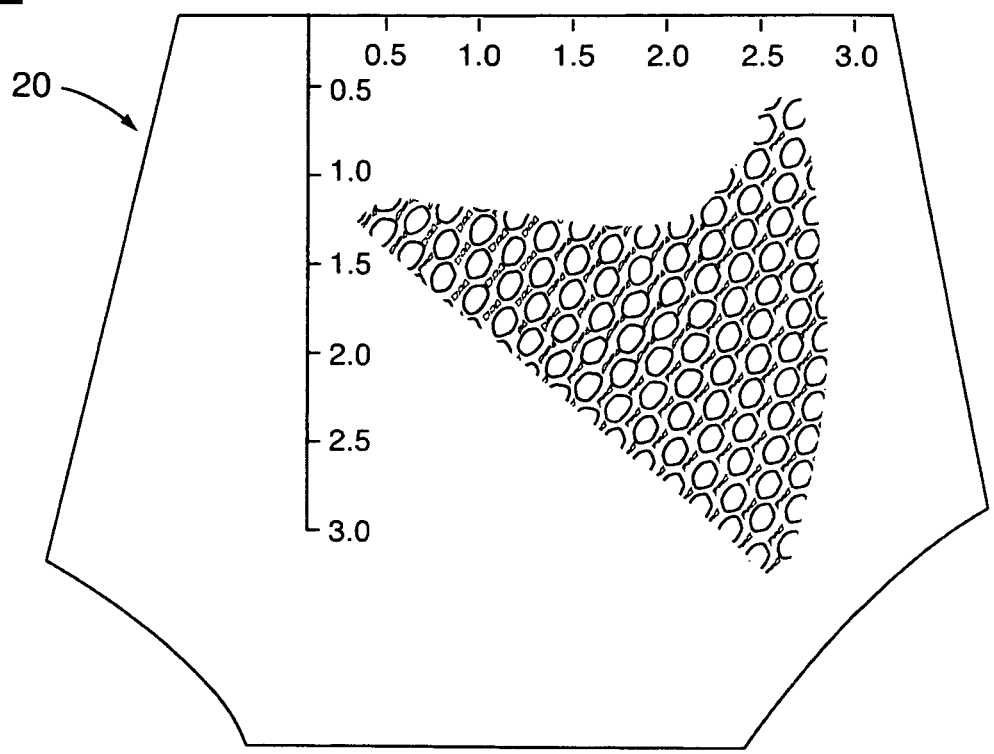
Figure 3:
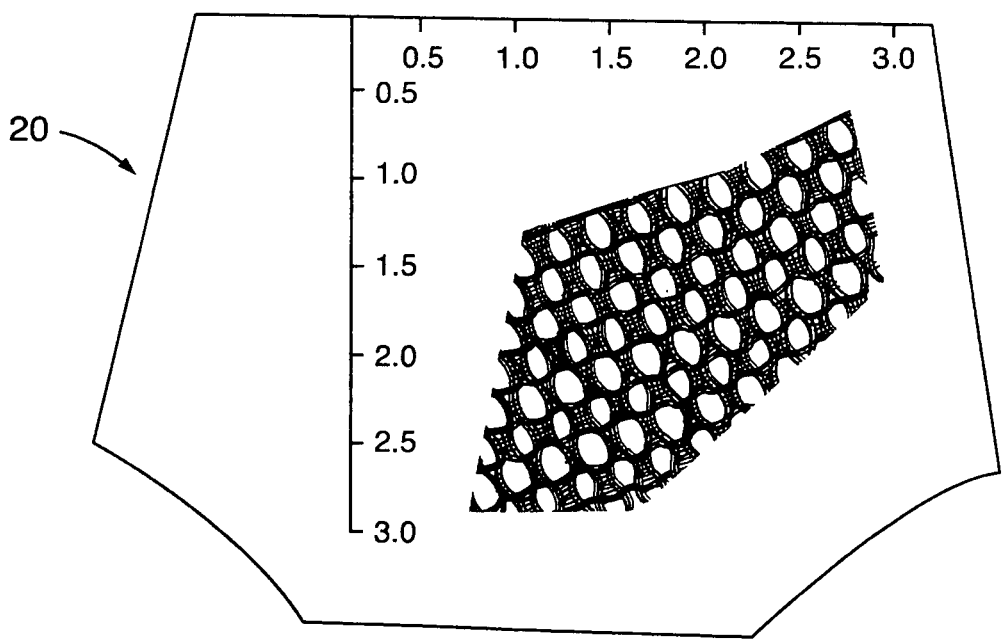
Figure 4:
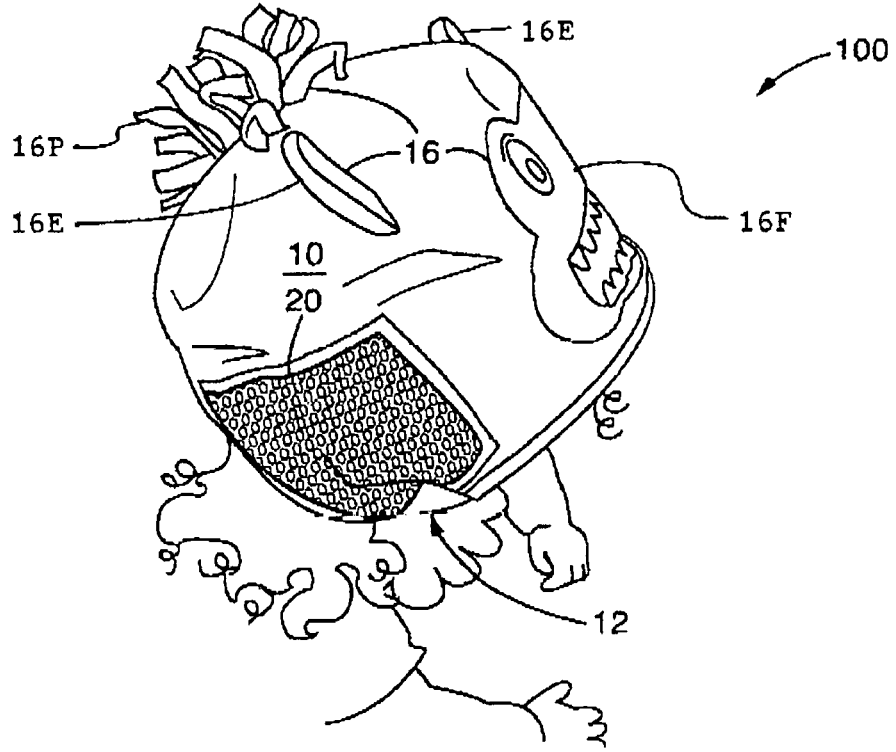
FIG. 4 is a right, top perspective view of a hat hereof for a child size 2-4T modeled by a doll and made of one external layer of fleece. Its soft, conforming open mesh to cover the external hardware of the cochlear implant is the preferred white mesh utility fabric mentioned with respect to FIG. 2.
Figure 5:
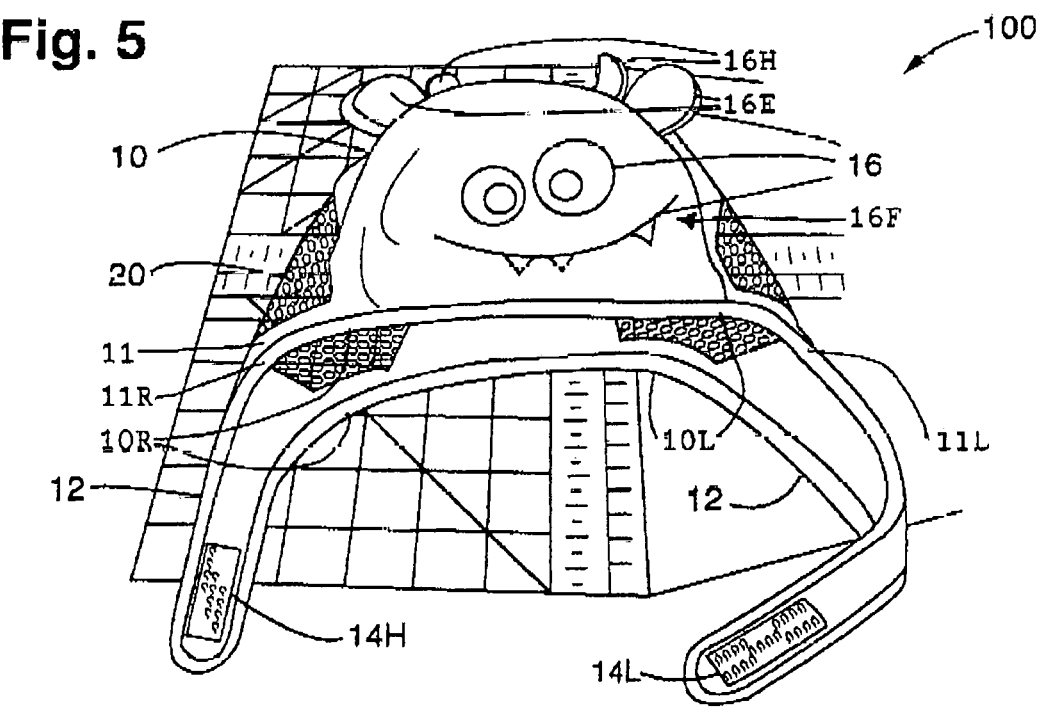
FIG. 5 is a front view of a hat hereof for a boy's size 8-18 months, made of one external layer of fleece. Its soft, conforming open mesh to cover the external hardware of the cochlear implant is the blue mesh utility fabric mentioned with respect to FIG. 3.
Figure 6:
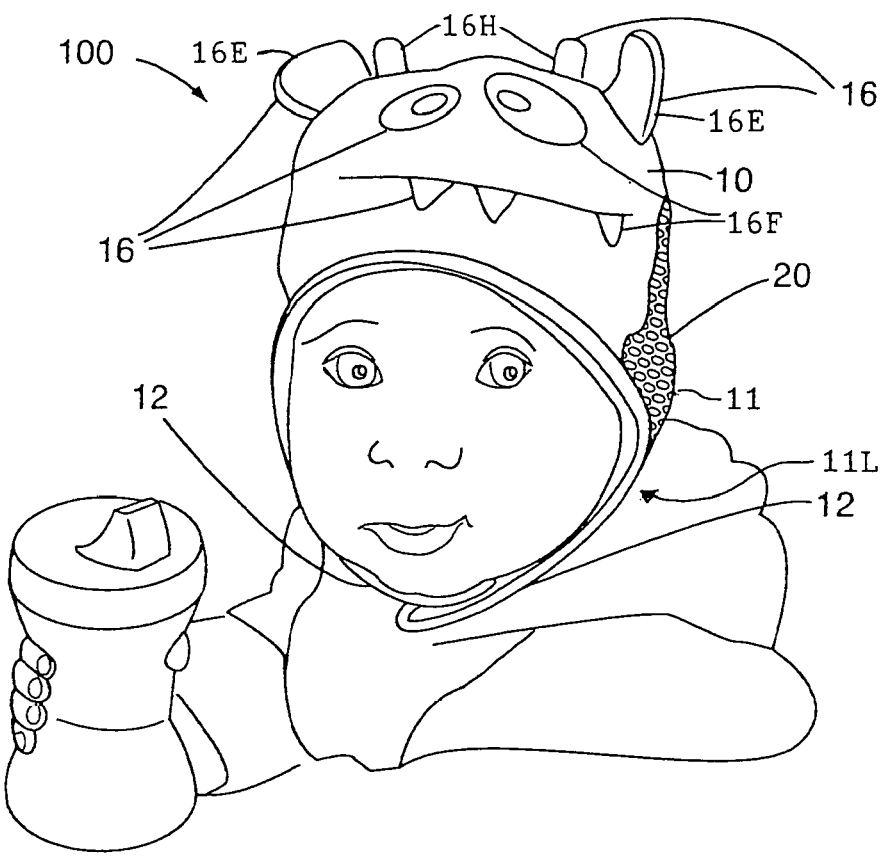
FIG. 6 is a front view, taken slightly from the left side, of the hat of FIG. 5, worn by a one-year old boy.
Figure 7:
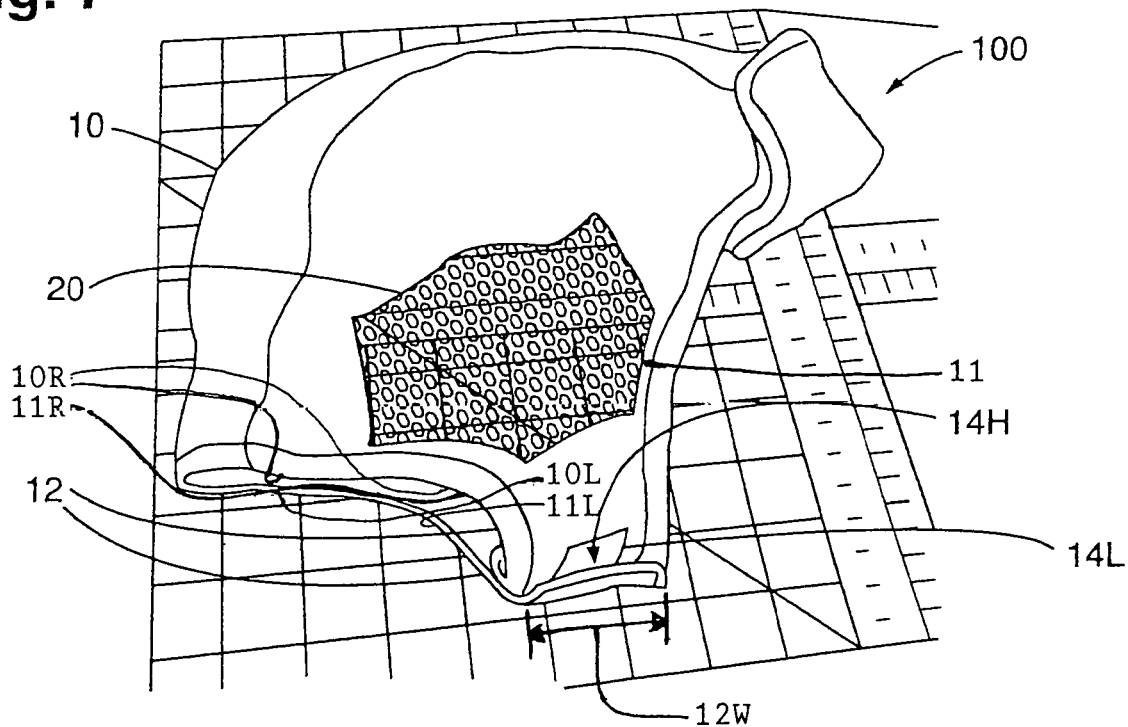
FIG. 7 is a right side view of a hat hereof. It features a different pattern for its soft, conforming open mesh to cover the external hardware of the cochlear implant, which, rather than having a straight top border, has a top border with a peak.
Figure 8:
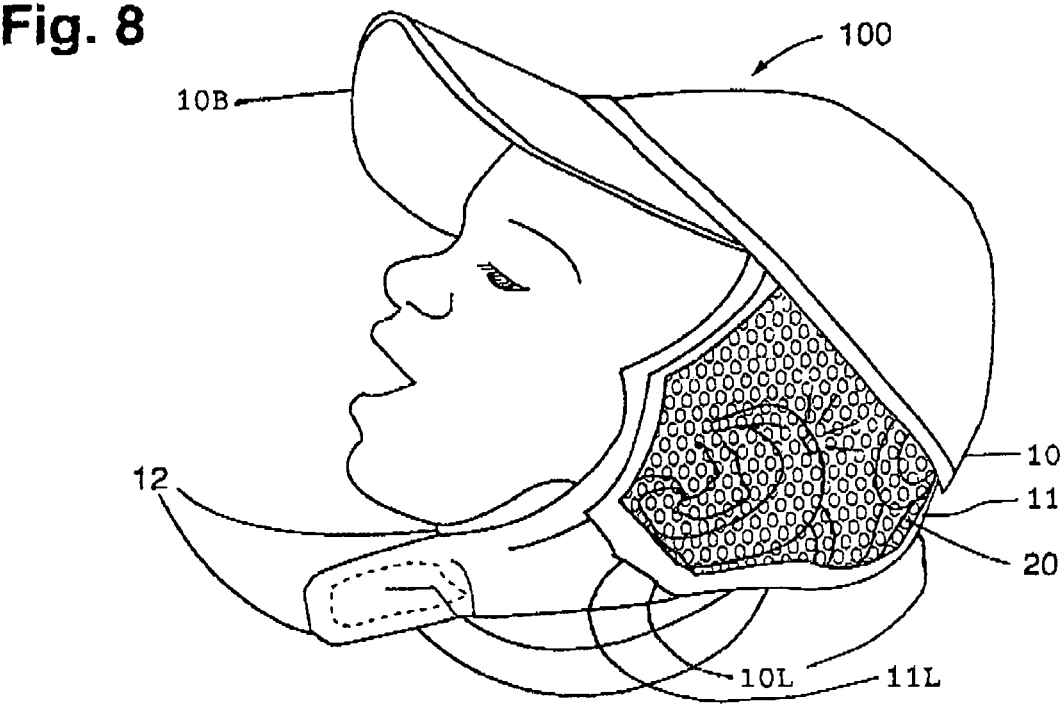
FIG. 8 is a left side view of a hat hereof. It is made by modifying an existing baseball cap, and shown being tried on by an about two-year old boy, with its straps not yet fastened together.
Figure 9:
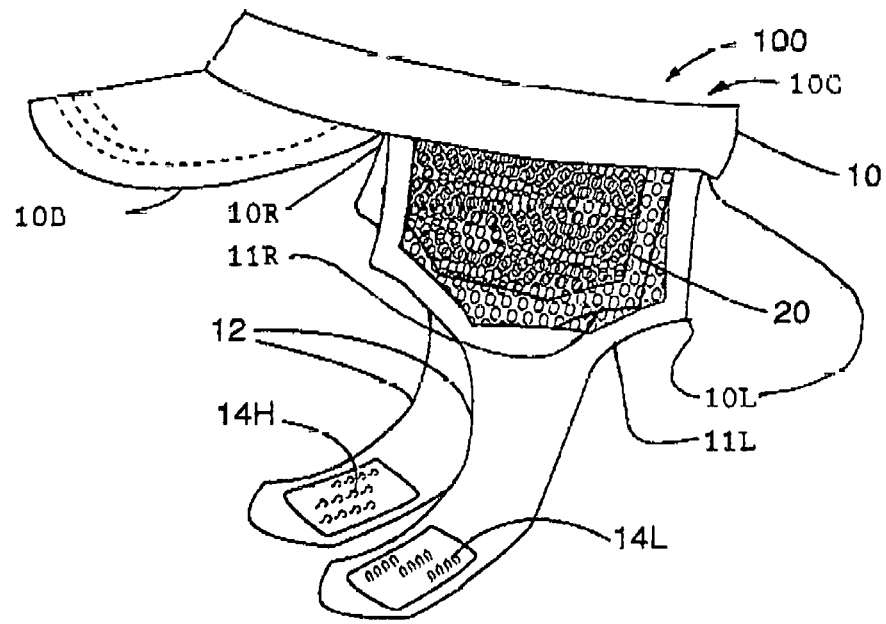
FIG. 9 is a left side view of a hat hereof. It is a cap with an open crown for wearing in warmer environments, here, including a bill such as in visor type headgear.

The hat 100 has left and/or right open mesh component(s) 20 to cover the external hardware of the cochlear implant and provide for securing it when worn by a wearer and for external visibility of the same by a non-wearer of the hat 100. FIGS. 2 and 3 have scales in inches, FIGS. 5 and 7 in centimeters and inches.

Testimonial examples are provided with reference to hat(s) as of FIGS. 1-7.

TESTIMONIAL EXAMPLE 1

As a mom of a 14-month-old child who received cochlear implants, I have to say these hats are the most wonderful invention. We have used the first hat that was made as a trial hat since it became available to us about two months after the surgery, and we now have many more that we use today! My son had an 8-hour surgery, and we thought that that was going to be the hardest part of the whole cochlear implant journey for our family, but I was wrong. Once my son had gotten the surgery he wouldn't leave the external hardware pieces on his head. It was next to impossible for me to get him to leave them on for even a minute. So, I wondered, how was he going to benefit from the miracle gift he was just given? My son would grab them, take them off, throw them, or at times even chew on them. Honestly, by the second day I was in tears trying to get my son to keep the external hardware pieces on, but all day long he would take them off the second the magnet touched his head. I would reapply them every time he took them off. It was very stressful. And how, I wondered, would he hear if he wouldn't leave them on?

That's when Grandma Cecelia decided to make a hat so that he would leave them on. She figured it was worth a try to help her grandson hear or benefit from the implants.

Grandma Cecelia did make a hat that did so much more than just keep the external hardware of the implants on and hold them in place. I can also see when the implant is connected to the external hardware and working by looking through the mesh material to the light on the processor, which will blink green so it can be seen easily. The mesh over the ear lets air in so battery packs do not get too warm. It allows the child to hear without a barrier between processor and the ear, so the microphone is right at ear level, and gives me peace of mind to know that he won't be throwing them off, losing them, or chewing on them because they are a very costly investment. The thought of replacing them is outrageous! Most of all, my son has a comfortable hat that will help him keep the external hardware of the implants on and in place so he can hear. There are no ties for him to pull on or bunch up under his chin—just a strap and a hook. These hats are colorful, fun and stylish, yet provide a great MIRACLE for parent and child. I know my son needs to wear cochlear implants, but because of his age he can't understand why wearing implants are so important. Again, the hat has provided my son to get the most from his cochlear implants because with the hat on he leaves them alone and I can actually relax and see that implants are working properly just by looking at the side of his head—how convenient! My son now wears his cochlear implants during all hours. He is awake thanks to these hats! I have proof they work like a charm because my son went from profound hearing loss to moderate hearing loss! This is possible because of the cochlear implant surgery and what I call the Miracle Hats. The key is wearing them. Now my son can do so, without so much worry!

Thank you so much for the marvelous invention. This will help many parents and children who are facing the same issues we did!

TESTIMONIAL EXAMPLE 2

I am a pediatric audiologist who works with hearing impaired children each day. Some of the pediatric population with whom I get to work have significant hearing loss and deafness, and they are eligible to get a cochlear implant. Cochlear implants are implantable devices placed within the cochlea, which enable deaf children to hear sound. The device includes an external magnetic device that attaches to the back of a child's head and an ear-level processor with microphones. This external device can be easily removed, and is often a source of difficulty for parents of infants and toddlers. Once children of this age become aware that the device can be removed, it becomes a source of entertainment for them.

With the innovative design of the hats created by Cecelia Marco, however, this issue has been resolved for parents of young children. The soft, breathable material, for example, is very comfortable for infants and toddlers to wear for extended periods of time without getting overheated. In addition, the microphones located on the processor are not obstructed owing to the unique mesh covering that allows sound to pass through. This is critical given that hearing impaired children need as much access to sound as possible when they are developing speech and language. Any barrier could create significant setbacks to their speech progress.

I strongly believe that these hats would provide a great service to children with cochlear implants during their early developmental years. Not only do they reduce stress for parents, but they are also very stylish and allow children to express their personalities.

CONCLUSION TO THE INVENTION

The present invention is thus provided. Various feature(s), part(s), subcombination(s) and/or combination(s) can be employed with or without reference to other feature(s), part(s), subcombination(s) and/or combination(s) in the practice of the invention, and numerous adaptations and modifications can be effected within its spirit, the literal claim scope of which is particularly pointed out as follows:

I claim:

1. A combination, which comprises a hat for securing external hardware of a cochlear implant or a traditional hearing aid of a wearer who has a head; and the external hardware of the cochlear implant or the traditional hearing aid wherein the hat comprises:
    a hat body of conforming material configured to cover and conform to at least a portion of the wearer's head and encircle the wearer's head about a forehead or crown portion of the wearer's head when the hat is worn by the wearer, including at least one depending projection portion on at least one side having a lower boundary that is configured to be lower than a location of a respective ear lobe of the wearer would be when the hat is worn by the wearer;
    an opposing pair of under-chin straps of conforming material attached to lower left and right boundaries of the hat body, the straps having a non-tying securing couple fixed to the under-chin straps for fastening the straps together, wherein the under-chin straps are configured to conform to the wearer's head under the chin when the hat is worn by the wearer and secured with the non-tying securing couple; and
    in part of the at least one depending projection portion, a conforming open mesh configured to cover the external hardware of the cochlear implant or the traditional hearing aid and provide for securing of the external hardware of the cochlear implant or the traditional hearing aid when worn by the wearer, to reduce it not avoid overheating of the external hardware of the cochlear implant or the traditional hearing aid, and to provide for external visibility of the external hardware of the cochlear implant or the traditional hearing aid of the wearer by a non-wearer of the hat when the hat and the external hardware of the cochlear implant or the traditional hearing aid of the wearer are worn by the wearer;
wherein the hat is configured to conform to the wearer's head and is such that the wearer is discouraged from inserting his or her hand under the hat and removing the external hardware of the cochlear implant or removing the traditional hearing aid; and the bat includes at least one of the following features A-E:
    A. the hat body and under-chin straps have their conforming material of fabric, which is a stretch fleece, and the under-chin straps are at least about one inch in width;
    B. the hat body and under-chin straps have their conforming material of fabric, which is stretch cotton, and the under-chin straps are at least about one inch in width;
    C. the hat body includes a bill;
    D. the hat body includes an open crown; and
    E. at least one feature selected from the group consisting of pom-poms and features representative of facial parts, ears, and horns.

2. The combination of claim 1, wherein the fabric is the stretch fleece.

3. The combination of claim 1, wherein the fabric is the stretch cotton.

4. The combination of claim 1, wherein the hat body includes the bill.

5. The combination of claim 1, wherein the hat body has the open crown.

6. The combination of claim 4, wherein the hat body has the open crown.

7. The combination of claim 1, which includes the at least one feature selected from the group consisting of pom-poms and features representative of facial parts, ears, and horns.

8. A combination, which comprises a hat for securing external hardware of a cochlear implant or a traditional hearing aid of a wearer who has a head; and the external hardware of the cochlear implant or the traditional hearing aid, wherein the hat comprises:
    a hat body of conforming material configured to cover and conform to at least a portion of the wearer's head and encircle the wearer's head about a forehead or crown portion of the wearer's head when the hat is worn by the wearer, including at least one depending projection portion on at least one side having a lower boundary that is configured to be lower than a location of a respective ear lobe of the wearer would be when the hat is worn by the wearer;
    an opposing pair of under-chin straps of conforming material attached to lower left and right boundaries of the hat body, the straps having a non-tying securing couple fixed to the under-chin straps for fastening the straps together, wherein the under-chin straps are configured to conform to the wearer's head under the chin when the hat is worn by the wearer and secured with the non-tying curing couple; and
    in part of the at least one depending projection portion, a conforming open mesh configured to cover the external hardware of the cochlear implant or the traditional hearing aid and provide for securing of the external hardware of the cochlear implant or the traditional hearing aid when worn by the wearer, to reduce if not avoid overheating of the external hardware of the cochlear implant or the traditional hearing aid, and to provide for external visibility of the external hardware of the cochlear implant or the traditional hearing aid of the wearer by a non-wearer of the hat when the hat and the external hardware cochlear implant or the traditional hearing aid of the wearer are worn by the wearer;
wherein the hat is configured to conform to the wearer's head and is such that the wearer is discouraged from inserting his or her hand under the hat and removing the external hardware of the cochlear implant or removing the traditional hearing aid; and the hat body has, as the at least one depending projection portion, a pair of opposing left and right side depending projection portions, a first depending projection portion on the left side and having a lower left boundary configured to be lower than a left ear lobe of the wearer, and a second depending projection portion on the right side and having a lower right boundary configured to be lower than a right ear lobe of the wearer.

9. The combination of claim 8, wherein the hat body is configured to span from front to back to cover the wearer's head from high forehead to crown to lower hairline/upper neck.

10. The combination of claim 8, wherein the hat body and under-chin straps have their conforming material of fabric, and the under-chin straps are at least about one inch in width.

11. The combination of claim 10, wherein the fabric is a stretch cotton.

12. The combination of claim 10, wherein the fabric is a stretch cotton.

13. The combination of claim 8, wherein the hat body includes a bill.

14. The combination of claim 8, wherein the hat body has an open crown.

15. The combination of claim 13, wherein the hat body has an open crown.

16. The combination of claim 8, wherein the hat includes at least one feature selected from the group consisting of pom-poms and features representative of facial parts, ears, and horns.

17. A method for securing external hardware of a cochlear implant or a traditional hearing aid of a wearer who has a head, the method comprising:
- providing the external hardware of the cochlear implant or a traditional hearing aid for the wearer;
- fitting the external hardware of the cochlear implant or a traditional hearing aid to the wearer;
- providing a hat for securing the external hardware of the cochlear implant or the traditional hearing aid of the wearer, wherein the hat includes:
  - a hat body of conforming material configured to cover and conform to at least a portion of the wearer's head and encircle the wearer's head about a forehead or crown portion of the wearer's head when the hat is worn by the wearer, including at least one depending projection portion on at least one side having a lower boundary that is configured to be lower than a location of a respective ear lobe of the wearer would be when the hat is worn by the wearer;
  - an opposing pair of under-chin straps of conforming material attached to lower left and right boundaries of the hat body, the under-chin straps having a non-tying securing couple fixed thereto for fastening the under-chin straps together, wherein the under-chin straps are configured to conform to the wearer's head under the chin when the hat is worn by the wearer and secured with the non-tying securing couple; and
  - in part of the at least one depending projection portion a conforming open mesh configured to cover the external hardware of the cochlear implant or the traditional hearing aid and provide for securing of the external hardware of the cochlear implant or the traditional hearing aid when worn by the wearer, to reduce if not avoid overheating of the external hardware of the cochlear implant or the traditional hearing aid, and to provide for external visibility of the external hardware of the cochlear implant or the traditional hearing aid of the wearer by a non-wearer of the hat when the hat and the external hardware of the cochlear implant or the traditional hearing aid of the wearer are worn by the wearer;
- wherein the hat is configured to conform to the wearer's head and is such that the wearer is discouraged from inserting his or her hand under the hat and removing the external hardware of the cochlear implant or removing the traditional hearing aid; and the hat includes at least one of the following features (A-F):
  - A. the hat body and under-chin straps have their conforming material of fabric, which is a stretch fleece, and the under-chin straps are at least about one inch in width;
  - B. the hat body and under-chin straps have their conforming material of fabric, which is a stretch cotton, and the under-chin straps are at least about one inch in width;
  - C. the hat body includes a bill;
  - D. the hat body includes an open crown; and
  - E. at least one feature selected from the group consisting of pom-poms and features representative of facial parts, ears, and horns; and
  - F. the hat body has, as the at least one depending projection portion, a pair of opposing left and right side depending projection portions, a first depending projection portion on the left side and having a lower left boundary configured to be lower than a left ear lobe of the wearer, and a second depending projection portion on the right side and having a lower right boundary configured to be lower than a right ear lobe of the wearer; and
- fitting the hat to, and securing the hat on the wearer.

18. The method of claim 17, wherein the wearer is a young child or otherwise another person with mental capabilities of a young child.

19. The method of claim 18, wherein the hat body has, as the at least one depending projection portion, the pair of opposing left and right side depending projection portions, the first depending projection portion on the left side and having the lower left boundary configured to be lower than the left ear lobe of the wearer, and the second depending projection portion on the right side and having the lower right boundary configured to be lower than the right ear lobe of the wearer.

* * * * *